United States Patent [19]

Johnson et al.

[11] Patent Number: 5,647,265

[45] Date of Patent: Jul. 15, 1997

[54] TOOL AND SYSTEM FOR MACHINING A ROUND STRAND

[75] Inventors: James T. Johnson, King George, Va.; Frank E. Kolstrom, Indian Head, Md.

[73] Assignee: The United States of America as represented by the Secretary of the Navy, Washington, D.C.

[21] Appl. No.: 84,057

[22] Filed: Jun. 30, 1993

[51] Int. Cl.$^6$ ................ B26D 3/00; G01N 1/04
[52] U.S. Cl. ................ 83/861; 83/123; 83/165; 83/167; 83/435.11; 83/451; 83/856; 83/919; 73/864.41
[58] Field of Search ................ 83/111, 123, 165, 83/451, 651, 856, 861, 875, 919, 686, 688, 689, 167, 435.11; 30/279.2, 280, 316; 73/864.41, 864.44, 864.45

[56] References Cited

U.S. PATENT DOCUMENTS

| | | | |
|---|---|---|---|
| 1,530,822 | 3/1925 | Gibson | 30/279.2 |
| 3,074,162 | 1/1963 | Lentini | 83/861 |
| 4,565,910 | 1/1986 | Peterson | 83/875 |
| 4,598,597 | 7/1986 | Widner et al. | 83/919 |
| 4,895,197 | 1/1990 | Andersen | 144/369 |
| 5,035,409 | 7/1991 | Mulliner | 269/21 |
| 5,048,804 | 9/1991 | Ito | 269/21 |
| 5,065,804 | 11/1991 | Kinuhata et al. | 83/875 |
| 5,103,684 | 4/1992 | Denton | 73/864.41 |
| 5,141,212 | 8/1992 | Beeding | 269/21 |
| 5,180,000 | 1/1993 | Wagner et al. | 165/80.1 |

FOREIGN PATENT DOCUMENTS

| | | | |
|---|---|---|---|
| 288014 | 4/1928 | United Kingdom | 30/316 |

*Primary Examiner*—Eugenia Jones
*Attorney, Agent, or Firm*—Jacob Shuster

[57] ABSTRACT

A system including a cutting tool is provided for cutting a round strand from a soft, rubber-based material. The cutting tool comprises a tube having an inner and an outer surface which form a sharp leading edge. The tool further comprises a blade which fixedly attaches to the outer surface of the cutting tube. The blade has a wedge-shaped leading edge and a circular-shaped arc on its bottom end for receiving the tube. A handle for the blade attaches to the top end of the blade. The system for cutting a round strand from a soft, rubber-based material also includes an arbor support arm, a vacuum chuck plate, and a horizontal milling machine having a numerical control. The arbor support arm connects to the handle of the cutting tool. The arbor support arm in turn connects to the horizontal milling machine. The vacuum chuck plate also connects to the horizontal milling machine at a table. The vacuum chuck plate has a cylindrical pin which extracts any round strands stuck in the cutting tube. The vacuum chuck plate also has a sloped surface for extracted round strands to roll into a collecting bin.

10 Claims, 5 Drawing Sheets

TOOL AND SYSTEM FOR MACHINING A ROUND STRAND

ORIGIN OF THE INVENTION

The invention described herein was made in the performance of official duties by an employee of the Department of the Navy and may be manufactured, used, licensed by or for the Government for any governmental purpose without payment of any royalties thereon.

FIELD OF THE INVENTION

The present invention relates generally to a cutting apparatus for soft materials and more particularly to a cutting apparatus having a cutting tube.

BACKGROUND OF THE INVENTION

Rubber-based propellants are typically tested for burning rate as part of quality control. This burning rate test involves the placement of a strand of the propellant in a cylindrical bomb and the ignition of the strand by a hot electrical wire. The test then records the start and stop times of the combustion of the strand over a specified distance. A burning rate may then be calculated.

Testing engineers have determined that cross-sectionally round or cylindrical strands of propellant provide better results in burning rate tests because round strands tend to combust more homogeneously from start to finish. Accordingly, engineers and technicians have sought methods for manufacturing or machining round strands of rubber-based propellants.

Related methods of machining strands of rubber-based propellants recognize safety precautions concerning the explosive nature of rubber-based propellants. These safety concerns require a technician operating a milling machine to control and observe the cutting of the propellant from a remote location. One example of remote operation involves a remotely-controlled guillotine cutter. The guillotine cutter simply cuts the soft propellant in two directions to provide a rectangularly-shaped strand. If the technician then wishes to produce a round strand, he must manually trim the corners of the rectangular strand. This method has two distinct disadvantages. First, the method requires the technician to come into physical contact with the propellant during cutting. This contact contradicts the recognized safety precautions normally followed during machining of rubber-based propellants. Second, the method includes an unautomated step of manual trimming, which increases the length of time necessary for machining a round strand.

Other cutting methods and devices of the related art include the belt skiving device of U.S. Pat. No. 4,656,910 by Peterson. Peterson discloses a device for cutting longitudinal channels or strips in the cover of a rubber conveyor belt. The device includes a U-shaped blade set at a specified angle relative to the surface of the conveyor belt. The U-shaped blade has a front portion with a sharp cutting edge. The blade cuts into the surface of the belt and removes rectangular, longitudinal strips.

SUMMARY OF THE INVENTION

Accordingly, an object of the present invention is to cut a round or cylindrical strand from a rubber-based propellant.

Another object is to machine a round strand safely from a rubber-based propellant.

Yet another object is to automate a system for machining round strands from a rubber-based propellant.

A further object of the invention is to lessen the time needed for machining a round strand from a rubber-based propellant.

The present invention attains the foregoing and additional objects by providing a tool and a system for cutting a round strand from a rubber-based material. The cutting tool comprises a tube, a blade, and a handle, preferably all made of stainless steel. The tube has an inner circumferential surface and an outer circumferential surface which forms a sharp leading edge. Alternatively, the tube has a second outer circumferential surface which combines with the first outer surface to form an obtuse angle at a point behind the sharp leading edge of the tube. The blade fixedly attaches to the first outer circumferential surface of the tube. The blade has a wedge-shaped leading edge and a circular-shaped arc on its bottom which is shaped for receiving the cutting tube. The leading edge of the blade attaches to the outer circumferential surface at a point behind the leading edge of the tube. Preferably, the blade also has a round trailing edge. The handle attaches to the top end of the blade.

The system for cutting a round strand from a rubber-based material includes the previously-described cutting tool, an arbor support arm, a vacuum chuck plate, and a horizontal milling machine having a numerical control. Preferably, the system further comprises a pump for pulling a vacuum in the chuck plate. The handle of the cutting tool includes an adjustable block assembly having a dovetail groove. The handle attaches to a dovetail of the arbor support arm. The arbor support arm connects to the horizontal milling machine. The horizontal milling machine also has a table for receiving the vacuum chuck plate. The vacuum chuck plate has a locating pin which extracts any round strand stuck in the tube. The vacuum chuck plate also has a sloped surface located near the locating pin for the finished round strand to roll into a collecting bin.

Still other objects and advantages of the present invention will become readily apparent to those skilled in the art from the following drawings and detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

DETAILED DESCRIPTION OF THE INVENTION

Figure 1:
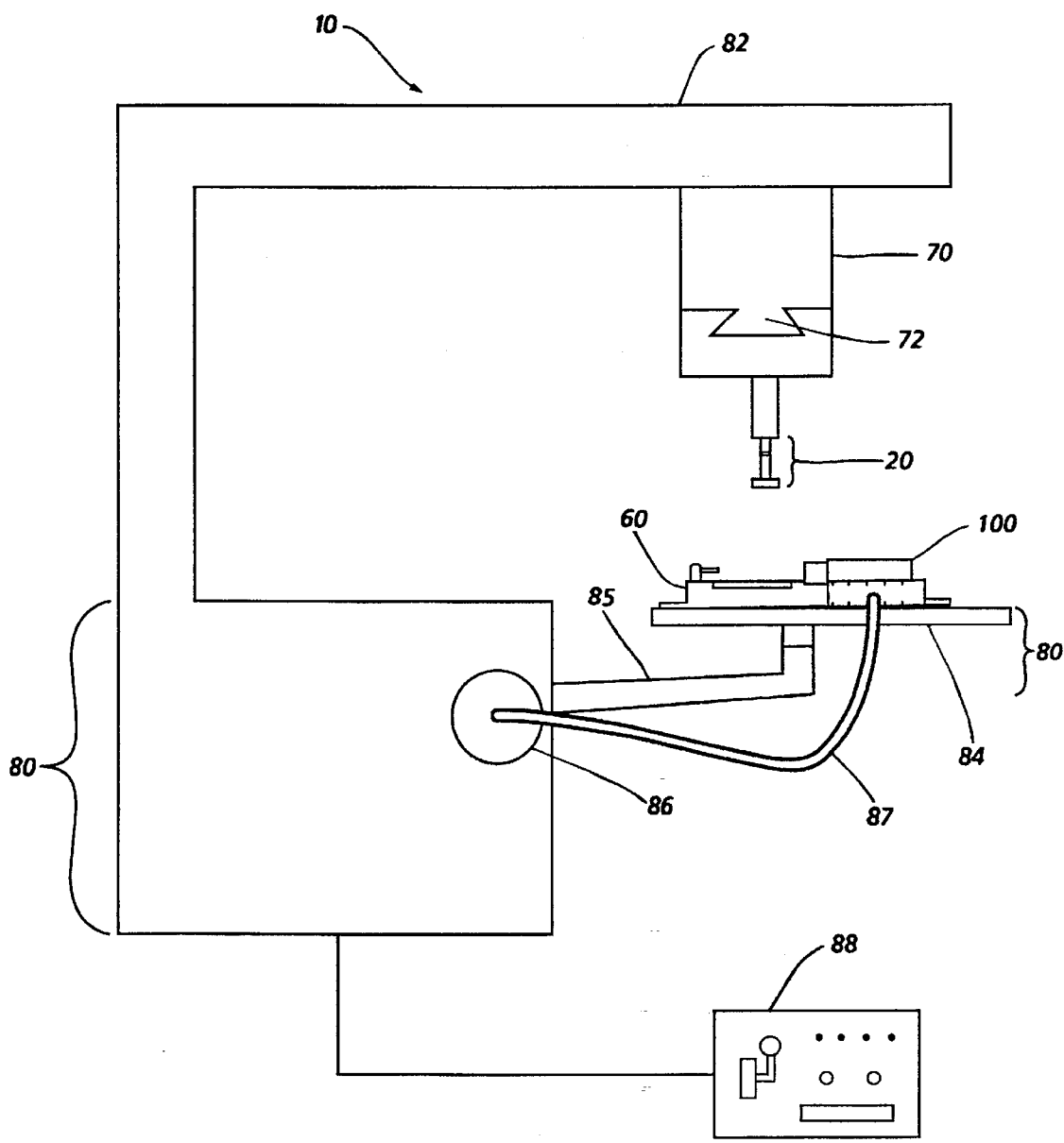
FIG. 1 illustrates a system for cutting a cylindrical strand from a rubber-based material.

Referring now to FIG. 1, a system 10 for cutting a round strand from a working sample of a rubber-based propellant 100 is shown. Round strand, as used in this specification, refers to a cylindrically-shaped segment of the propellant. The system 10 comprises a cutting tool 20, a vacuum chuck plate 60, an arbor support arm 70, and a horizontal milling machine 80, the horizontal milling machine being generally known in the art. The cutting tool 20 connects to a dovetail 72 of the arbor support arm 70, which in turn connects to a support bar 82 of the milling machine 80. The vacuum chuck plate 60 connects to a table 84 of the milling machine. The table 84 is positioned under the cutting tool 20.

The milling machine 80 has a vacuum pump 86 and a numerical control 88 for both remote and automatic operation of the system. The vacuum pump 86, connected to vacuum chuck plate 60 by flexible line 87, is one commonly known in the art such as the Stokes Microvac which can pull a vacuum of 40 cubic feet per minute. The numerical control 88 is a standard numerical control system as is commonly known in the art of milling machines, such as the A.I.T. horizontal mill. During its operation, the milling machine using table support arm 85 moves the table 84 into various positions, in a manner known in the art, while the cutting tool 20 remains stationary above the vacuum chuck plate 60 and the working sample 100. Alternatively, the arbor support arm 70 may maneuver the cutting tool 20 into the working material to perform the cuts.

Figure 2A:
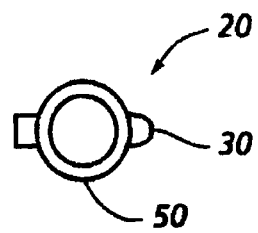
FIGS. 2A, 2B, and 2C are top, front, and side views, respectively, of a cutting tool in accordance with the present invention.
Figure 2B:
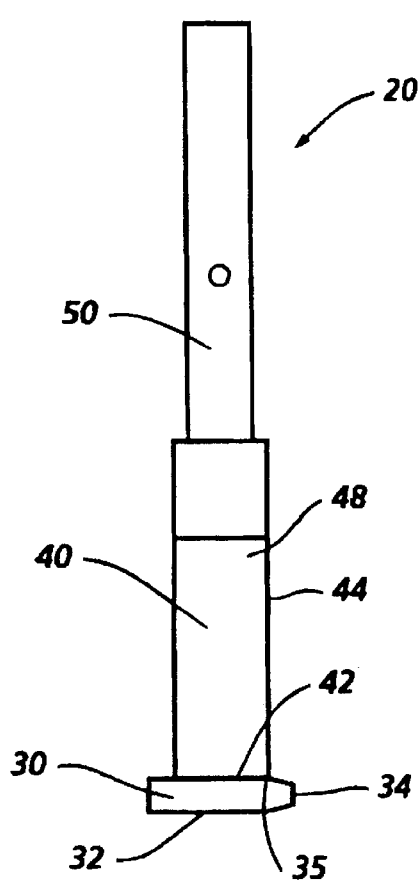
Figure 2C:
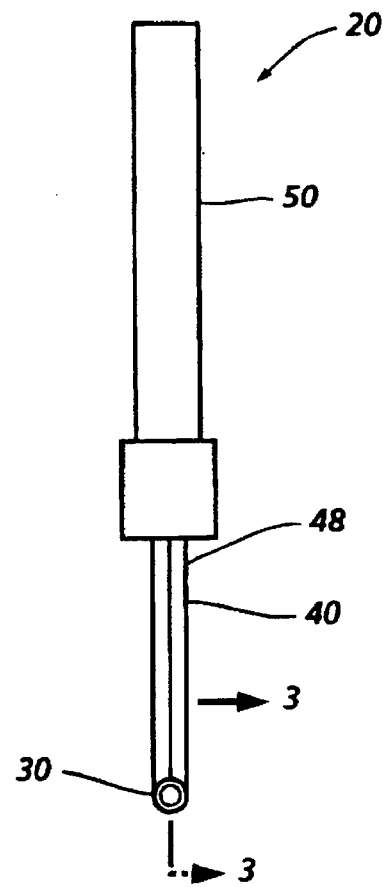

As shown in FIGS. 2A–2C, the cutting tool 20 comprises a tube 30, a blade 40, and a handle 50. Preferably, the tube, the blade and the handle are made of stainless steel. As shown in FIG. 2B, the tube has an outer circumferential surface 32 and a leading edge 34. The blade 40 fixedly attaches to the outer circumferential surface 32 of the tube at a bottom end 42 of the blade. The blade 40 also has a leading edge 44. The leading edge 44 of the blade attaches to the outer circumferential surface 32 of the tube 30 at a point 35 which is behind the leading edge 34 of the tube. As shown in FIG. 2B and FIG. 2C, the handle 50 is a tubular extension which fixedly attaches to a top end 48 of the blade.

Figure 3:
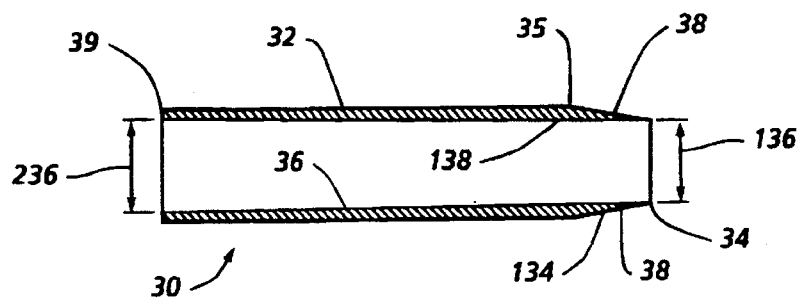
FIG. 3 is a cross-sectional view of the tube along line 3—3 of FIG. 2C.

As seen in FIG. 3, the tube 30 has an inner circumferential surface 36 and a second outer circumferential surface 38. The inner surface 36 and second outer surface 32 form an acute angle 134 and give the tube the sharp leading edge 34. The sharp leading edge enables the tube 30 to cut easily into the soft working sample of rubber-based propellant. The tube 30 also has a first inner diameter 136 at the leading edge 34 and a second inner diameter 236 at a trailing edge 39. The first inner diameter 136 is slightly smaller than the second inner diameter 236. The slight expansion of the inner diameters of the tube assists the tube in passing through the working sample.

The second outer circumferential surface 38 intersects with the first outer surface 32 at a plurality of points 35 to form a plurality of obtuse angles 138 which are behind the sharp leading edge 34 of the tube. Each obtuse angle 138 has a vertex on the line of points 35 at which the leading edge 44 of blade 40 is attached to the outer circumferential surface 32 of tube 30 as shown previously in FIG. 2B.

Figure 4A:
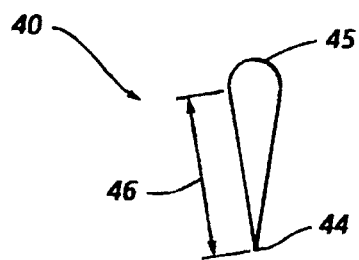
FIGS. 4A and 4B are top and front views, respectively, of a blade of the cutting tool.
Figure 4B:
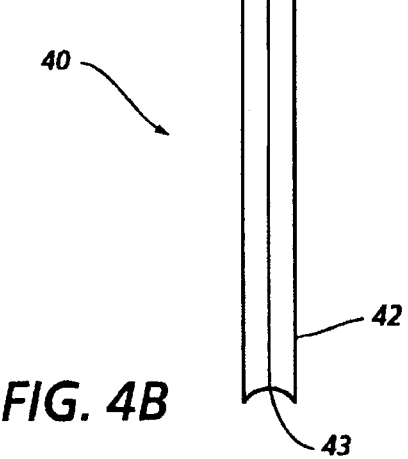

FIG. 4A illustrates the blade 40 has a wedge-shape 46 for the leading edge 44 and a round trailing edge 45. Referring to FIG. 4B, a circular-shaped arc 43, located at the bottom end 42 of the blade is fitted for receiving the tube.

Placing the blade behind the leading edge of the tube enables the tube to make a first cylindrical cut into the working sample. As the tube then continues to cut through the sample, the blade makes a second cut which, because of the wedge shape of the blade, separates the upper surface and spreads the side surfaces of the sample. Accordingly, the blade assists the cutting action of the tube by reducing the surface tension on the working sample.

Figure 5A:
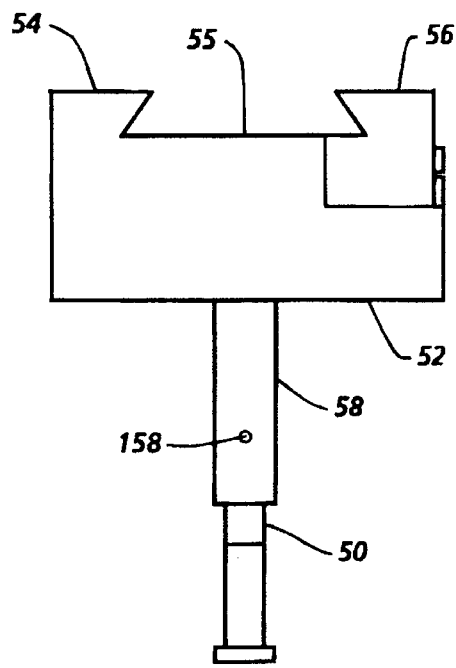
FIGS. 5A and 5B are front and side views of the cutting tool having an adjustable block assembly.
Figure 5B:
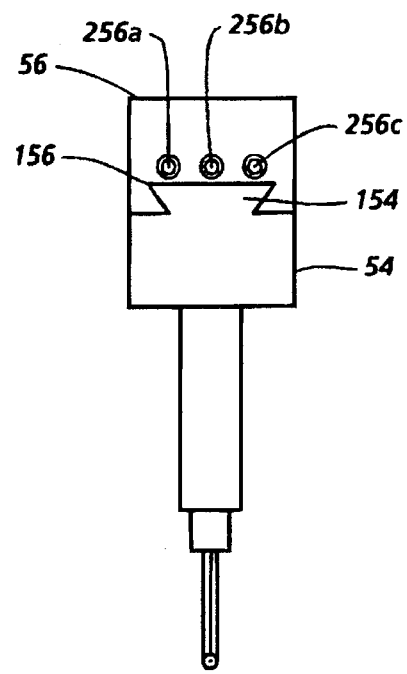

Referring now to FIG. 5A, an adjustable block assembly 52 comprises a main block 54, an adjustable block 56, and a socket 58. The main block and the adjustable block combine to form a dovetail groove 55. The handle 50 of the cutting tool inserts into the socket 58 and is fixedly attached by a locking pin or screw 158. The adjustable block assembly accordingly attaches to the dovetail 72 of the arbor support arm shown in FIG. 1. Referring now to FIG. 5B, the main block 54 has its own dovetail 154 and the adjustable block 56 has its own dovetail groove 156. The adjustable block 56 slides onto the dovetail 154 and then fixedly attaches to the main block 54 by three socket head cap screws 256a–c.

Figure 6:
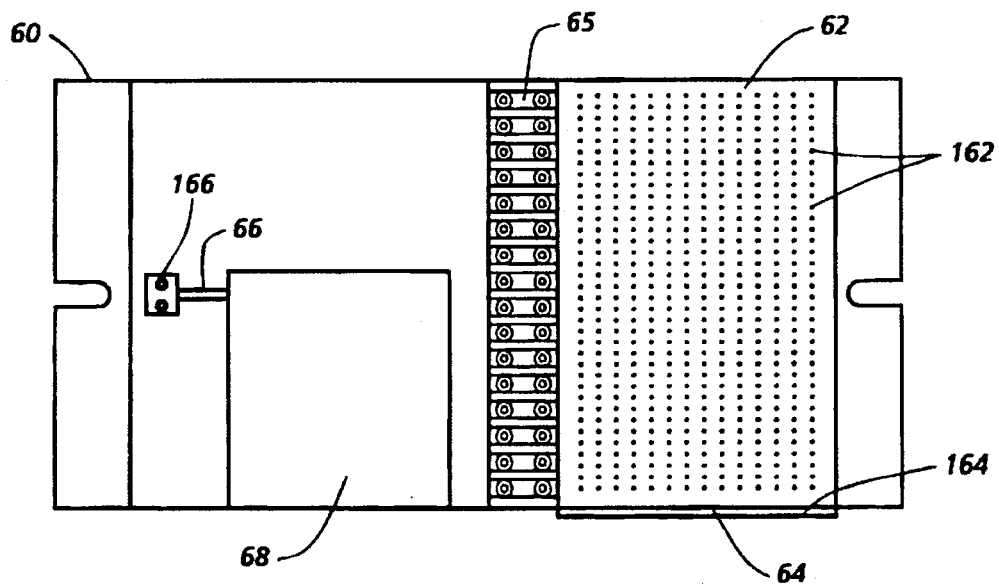
FIG. 6 is a top view of a vacuum chuck plate of the present invention.

As shown in FIG. 6, the vacuum chuck plate 60, which is preferably made of aluminum, has a flat surface 62 with a plurality of small-sized holes 162 and a manifold 64 which includes a gasket (not shown) and a cover plate 164. The manifold 64 has a plurality of bores (not shown) which are in direct communication with the plurality of small-sized holes 162. The chuck plate 60 also comprises a locating pin 66 which connects to a locating block 166.

Figure 7:
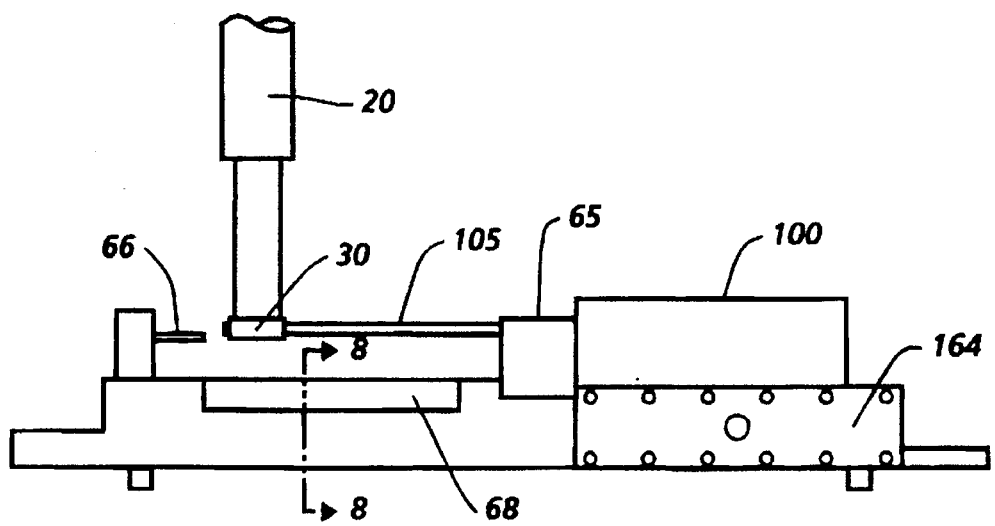
FIG. 7 illustrates a cutting tool having a cut round strand in accordance with the present invention.

Referring now to FIGS. 6 and 7, the vacuum pump of the milling machine pulls a vacuum through the plurality of bores of the chuck plate 60 and, in turn, the holes 162. This vacuum creates a lower pressure at the flat surface 62 upon which the working sample 100 sits. The lower pressure on the bottom surface of the working sample combines with the relatively higher pressure on the remaining surfaces of the sample to secure it during milling operations.

As shown in FIGS. 6 and 7, the cutting tool 20 is positioned with its leading edge 34 adjacent the locating pin 66 in order to remove a round cylindrical strand 105 from the working sample 100. The cylindrical strand typically remains imbedded in the tube 30 after being cut. Accordingly, the locating pin 66 is displaced relative to the tube 30 by operation of the milling machine in a manner known in the art to thereby push and extract the cut strand 105 from the tube 30.

Figure 8:
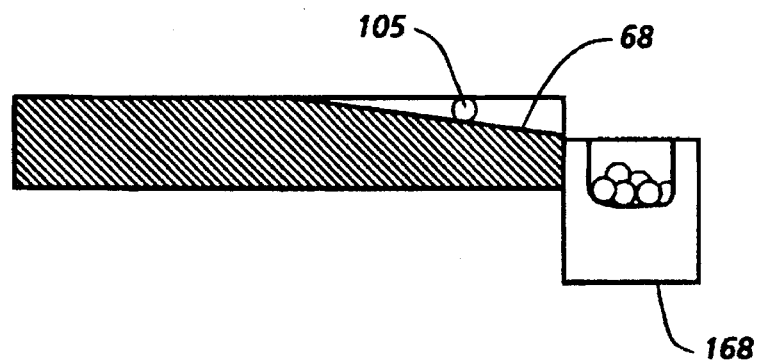
FIG. 8 is a cross-sectional view of the vacuum chuck plate along line 8—8 of FIG. 7.

After being pushed out of the tube, the round strand falls onto a sloped surface 68. As shown in FIG. 8, the strand 105 then rolls down the surface 68 into a collecting bin 168.

Figure 9:
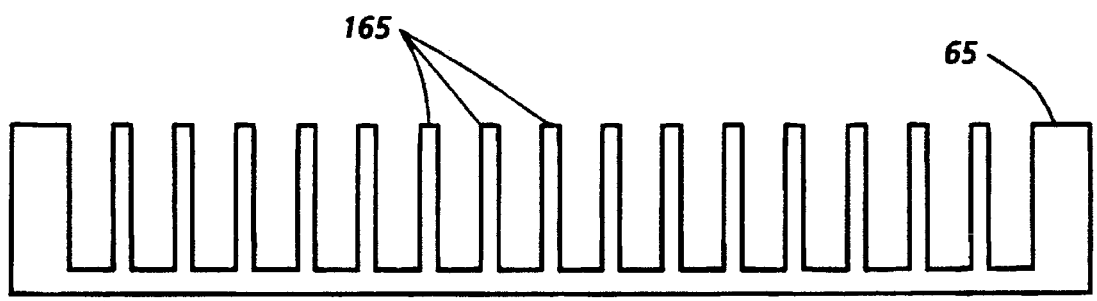
FIG. 9 is a side view of a spacing rack in accordance with the present invention.

As seen in FIGS. 6 and 9, the vacuum chuck plate also has a rack 65 having a plurality of spacing juts 165. The juts assist in spacing and aligning a cut round strand as the cutting tool moves toward the locating pin.

The unique features of this invention include a cutting tool having a tube with a sharp leading edge and a wedge-shaped blade with a circular-shaped arc on the bottom end. The cutting tool also has the leading edge of the blade begin at a point behind the sharp leading edge of the tube. Other unique features include a vacuum chuck plate having a locating pin which extracts a cut round strand from the tube and a sloped surface for transporting or rolling the extracted round strand into a collecting bin.

The advantages of this invention include the ability to machine a round strand from one pass through a rubber-based propellant. Other advantages include reducing the time needed to machine a round strand and eliminating a technician's physical contact with the propellant during the cutting process. Yet other advantages include automating the entire cutting of the rubber-based propellant.

Although the invention has been described relative to a specific embodiment thereof, there are numerous variations and modifications that will be readily apparent to those skilled in the art in the light of the above teachings. It is therefore to be understood that, within the scope of the appended claims, the invention may be practiced other than as specifically described.

What is claimed as new and desired to be secured by Letters Patent of the United States is:

1. In a system having a milling machine for cutting a cylindrical strand from a rubber-based material, the improvement comprising:

a tube having an outer circumferential surface and a sharp leading edge;

a blade having a top end and a bottom end and being fixedly attached to the outer circumferential surface of said tube at the bottom end of said blade, said blade also having a wedge-shaped leading edge and a circular-shaped arc on the bottom end for receiving said tube;

a handle connected to the top end of said blade;

an arbor support arm connecting said handle to the milling machine which has a moveable table and a vacuum chuck plate attached to said moveable table on which the rubber-based material is carried.

2. In a system for cutting a cylindrical strand from a rubber-based material, as recited in claim 1 wherein said handle includes an adjustable block assembly having a dovetail groove.

3. In a system for cutting a cylindrical strand from a rubber-based material as recited in claim 2 wherein said arbor support arm has a dove tail for securely holding the adjustable block assembly of said handle.

4. In a system for cutting a cylindrical strand from rubber-based material as recited in claim 1 wherein said vacuum chuck plate mounts a locating pin for extracting the cylindrical strand from said tube.

5. In a system for cutting a cylindrical strand from a rubber-based material as recited in claim 1 wherein said vacuum chuck plate includes a sloped surface for transporting the extracted cylindrical strand.

6. In a system for cutting a cylindrical strand from rubber-based material as recited in claim 1 wherein said vacuum chuck plate includes a rack having a plurality of juts for spacing a plurality of cut cylindrical strands.

7. In a system for cutting a cylindrical strand from rubber-based material as recited in claim 1 wherein said vacuum chuck plate has a flat outer surface with a plurality of suction holes.

8. In a system for cutting a cylindrical strand from a rubber-based material as recited in claim 1 wherein said vacuum chuck plate is made of aluminum.

9. In a system for cutting a cylindrical strand from a rubber-based material as recited in claim 1 further comprising a numerical control for remotely and automatically operating the system.

10. In a system for cutting a cylindrical strand from a rubber-based material as recited in claim 1 further comprising a vacuum pump for pulling a vacuum in said vacuum chuck plate.

* * * * *